United States Patent [19]

Buckley

[11] Patent Number: 6,103,242
[45] Date of Patent: Aug. 15, 2000

[54] METHOD OF CONTROLLING BLOOD SUGAR LEVELS USING *COCCOLOBA UVIFERA*

[76] Inventor: William Buckley, 7302 Daggett Ter., New Port Richey, Fla. 34655

[21] Appl. No.: 09/422,761

[22] Filed: Oct. 21, 1999

[51] Int. Cl.[7] .................................................. A61K 35/78
[52] U.S. Cl. ........................................................ 424/195.1
[58] Field of Search ........................................... 424/195.1

[56] References Cited

U.S. PATENT DOCUMENTS

| | | |
|---|---|---|
| 4,288,244 | 9/1981 | Kirino et al. . |
| 4,657,581 | 4/1987 | Takematsu et al. . |
| 4,883,651 | 11/1989 | Meyer . |
| 5,837,257 | 11/1998 | Tsai et al. . |
| 5,886,029 | 3/1999 | Dhaliwal . |

OTHER PUBLICATIONS

Kim et al., Archives of Pharmacal Research (Seoul), vol. 19, No. 6, pp. 441–446, 1996.
Lin et al., Journal of the Formosa Medical Association, vol. 66, No. 2, pp. 58–66, 1967.
Malathi et al., Fitoterapia, vol. 66, No. 3, p. 277, 1995.
Agricultural Research Service, *Coccoloba uvifera* (Polygonaceae, http://www.ars–grin.gov, Oct. 8, 1999.
EthnobotDB home page, Taxon: *Coccoloba uvifera*, http://ars–genome.cornell.edu, Oct. 3, 1999.
American Diabetes Association, The Dangerous Tolls of Diabetes, http://www.diabetes.org, Jan. 19, 2000.
Raintree Nutrition, Inc., *Petiveria alliacea*, http://rain–tree.com, Jan. 19, 2000.
Raintree Nutrition, Inc., *Cynara scolymus*, http://rain–tree.com, Jan. 19, 2000.
Raintree Nutrition, Inc., *Ageratum conyzoides*, http://rain–tree.com, Jan. 19, 2000.
Raintree Nutrition, Inc., *Medicago sativa*, http://rain–tree.com, Jan. 19, 2000.
Raintree Nutrition, Inc., *Anacardium occidentale*, http://rain–tree.com, Jan. 19, 2000.
Raintree Nutrition, Inc., *Uncaria tomentosa, guianensis*, http://rain–tree.com, Jan. 19, 2000.
Raintree Nutrition, Inc., *Theobroma cacao*, http://rain–tree.com, Jan. 19, 2000.
Raintree Nutrition, Inc., *Mirabilis jalapa*, http://rain–tree.com, Jan. 19, 2000.
Raintree Nutrition, Inc., *Zea mays*, http://rain–tree.com, Jan. 19, 2000.
Raintree Nutrition, Inc., *Saussurea Iappa*, http://rain–tree.com, Jan. 19, 2000.
Raintree Nutrition, Inc., *Turnera diffusa, aphrodisiaca*, http://rain–tree.com, Jan. 19, 2000.
Raintree Nutrition, Inc., *Angelica sinensis*, http://rain–tree.com, Jan. 19, 2000.
Raintree Nutrition, Inc., *Boerhaavia diffusa, hirsuta*, http://rain–tree.com, Jan. 19, 2000.
Raintree Nutrition, Inc., *Foeniculum vulgare*, http://rain–tree.com, Jan. 19, 2000.
Raintree Nutrition, Inc., *Annona muricata*, http://rain–tree.com, Jan. 19, 2000.
Raintree Nutrition, Inc., *Equisetum arvense*, http://rain–tree.com, Jan. 19, 2000.
Raintree Nutrition, Inc., *Hymenaea courbaril*, http://rain–tree.com, Jan. 19, 2000.
Raintree Nutrition, Inc., *Glycyrrhiza glabra*, http://rain–tree.com, Jan. 19, 2000.
Raintree Nutrition, Inc., *Guazuma ulmifolia*, http://rain–tree.com, Jan. 19, 2000.
Raintree Nutrition, Inc., *Mucuna pruriens*, http://rain–tree.com, Jan. 19, 2000.
Raintree Nutrition, Inc., *Tabebuia heptaphylla, impetiginosa, avellanedae*, http://rain–tree.com, Jan. 19, 2000.
Raintree Nutrition, Inc., *Vinca minor.major*, http://rain–tree.com, Jan. 19, 2000.
Raintree Nutrition, Inc., *Ptychopetalum olacoides*, http://rain–tree.com, Jan. 19, 2000.
Raintree Nutrition, Inc., *Trichosanthes kirilowii*, http://rain–tree.com, Jan. 19, 2000.
Raintree Nutrition, Inc., *Smilax officinalis*, http://rain–tree.com, Jan. 19, 2000.
Raintree Nutrition, Inc., *Polypodium lepidopteris, decumanum*, http://rain–tree.com, Jan. 19, 2000.
Raintree Nutrition, Inc., *Rehmannia glutinosa*, http://rain–tree.com, Jan. 19, 2000.
Raintree Nutrition, Inc., *Baccharis genistelloides*, http://rain–tree.com, Jan. 19, 2000.
Raintree Nutrition, Inc., *Brunfelsia uniflorus, grandiflora*, http://rain–tree.com, Jan. 19, 2000.
Raintree Nutrition, Inc., *Stevia rebaudiana*, http://rain–tree.com, Jan. 19, 2000.
Raintree Nutrition, Inc., *Bixa orellana*, http://rain–tree.com, Jan. 19, 2000.

(List continued on next page.)

*Primary Examiner*—Francisco Prats
*Assistant Examiner*—Susan D. Coe
*Attorney, Agent, or Firm*—Anton J. Hopen; Smith & Hopen, P.A.

[57] ABSTRACT

A method of treating diabetes in a patient comprising the steps of administering a first quantity of an ingestible medium of *coccoloba uvifera* leaf extract to the patient, monitoring the patient's change in serum glucose level, and modifying, if needed, the first quantity of the ingestible medium of *coccoloba uvifera* leaf extract wherein the patient's serum glucose level is reduced to normal levels. Normal levels are generally considered to be about 110 to 130 mg serum glucose per liter. Accordingly, monitoring and adjustment in the dosages of the ingestible medium of *coccoloba uvifera* leaf extract are increased until the patient's serum glucose level is reduced to 130 mg per liter or less. The patient's serum glucose level may be monitored daily or twice daily depending on the severity of the patient's condition. While the ingestible medium of *coccoloba uvifera* leaf may be ingested daily, dosages may be staggered to several times a week provided the patient's condition is properly monitored.

20 Claims, No Drawings

OTHER PUBLICATIONS

Florida Dept. of Agriculturee and Consumer Services, "Sea Grape *(Coccoloba uvifera)*," Seagrape, 1st ed., http://www.fl–ag.com/forest/seagrape.htm (Tallahassee, Florida), (Oct. 21, 1997).

R.L. Philips and Gene Joyner, "The Seagrape," University of Florida Institute of Food and Agricultural Sciences, http://www.floridaplants.com/horticulture/seagrape.htm (Gainesville, Alachua County), Feb. 15, 1999.

Cornell University, "Taxon: *Coccoloba uvifers*," EthnobotDB, http://ars–genome.cornell.edu, Oct. 3, 1999.

METHOD OF CONTROLLING BLOOD SUGAR LEVELS USING *COCCOLOBA UVIFERA*

FIELD OF INVENTION

The present invention relates generally to a method of controlling blood sugar levels in diabetics, and more particularly to treatment with compounds derived from *coccoloba uvifera*.

BACKGROUND OF THE INVENTION

This invention is direct to a treatment for diabetes mellitus. Diabetes mellitus is a disease in which the pancreas produces little or no insulin, a hormone that helps the body's tissues absorb glucose (sugar) so it can be used as a source of energy. In people with diabetes, glucose levels build up in the blood and urine, causing excessive urination, thirst, hunger and problems with fat and protein metabolism.

In the United States, about 16 million people suffer from diabetes mellitus, although only half of these individuals have been diagnosed. Every year, about 650,000 people learn they have the disease. Diabetes mellitus is the seventh leading cause of all deaths and the sixth leading cause of all disease-caused deaths.

Without an appropriate level of insulin to help absorption, glucose levels increase in the blood because it cannot enter the cells. When the blood passes through the kidneys, organs that remove blood impurities, the kidneys cannot absorb the excess glucose. This excess glucose enters into the urine causing frequent urination to get rid of the additional water drawn into the urine. Excessive thirst occurs to trigger replacement of lost water in addition to added hunger to replace the glucose lost in urination. Additional symptoms include blurred vision, dramatic weight loss, irritability, weakness and fatigue, and nausea and vomiting.

Diabetes is classified into two types. Type 1 is known as immune-mediated diabetes (formerly called insulin-dependent diabetes). An estimated 500,000 to 1 million people in the United States have this type of diabetes. Type 1 diabetes destroys the cells in the pancreas that produce insulin, usually leading to a total failure to produce insulin. It typically starts in children or young adults who are slim, but can start at any age. Untreated Type 1 diabetes affects the metabolism of fat. Because the body cannot convert glucose into energy, it begins to break down stored fat for fuel. This produces increasing amounts of acidic compounds called ketone bodies in the blood, which interfere with respiration. People with Type 1 diabetes must give themselves at least one shot of insulin every day. Individuals with Type 1 diabetes measure the level of glucose in a drop of their blood obtained by pricking a fingertip.

In Type 2 diabetes, or non-insulin-dependent diabetes mellitus, (formerly called adult-onset diabetes), the body either makes insufficient amounts of insulin or is unable to use it. Type 2 diabetes often develops slowly. Most people who get it have increased thirst and an increased need to urinate. Many also feel edgy, tired and sick to their stomach. Some people have an increased appetite, but they lose weight. Other signs include repeated or hard-to-heal infections of the skin, gums, vagina or bladder; blurred vision; tingling or loss of feeling in the hands or feet; and dry, itchy skin.

Type 2 diabetes accounts for 90 to 95 percent of all cases of diagnosed diabetes in the United States. Each year nearly 600,000 new cases are diagnosed. The onset of Type 2 diabetes usually occurs after the age of 40 and often after the age of 55. Type 2 diabetes is known to cause problems with the kidneys, legs and feet, eyes, heart, nerves and blood flow.

If left untreated, Type 1 diabetes can result in diabetic coma (a state of unconsciousness caused by extremely high levels of glucose in the blood) or death. In both Type 1 and Type 2 diabetes, blood sugar, blood pressure, and blood fats must be well-controlled to prevent possible development of blindness, kidney failure, and heart disease. Also, tiny blood vessels in the body may become blocked-a dangerous complication. When blood vessels of the eye are affected, it can result in retinopathy, the breakdown of the lining at the back of the eye. When the kidney is affected it is called nephropathy, the inability of the kidney to properly filter body toxins.

According to the American Diabetes Association®), the total annual economic cost of diabetes in 1997 was estimated to be $98 billion dollars. That includes $44.1 billion in direct medical and treatment costs and $54 billion for indirect costs attributed to disability and mortality. In 1997, total health expenditures incurred by people with diabetes amounted to $77.7 billion, including health care costs not resulting from diabetes. The per capita costs of health care for people with diabetes amounted to $10,071 while health care costs for people without diabetes amounted to $2,699 in 1997.

In an effort to provide a natural source of insulin, some patients have received pancreas transplants. These patients must receive immunosupressant drugs to prevent their body from rejecting the new pancreas. However, the side effects of these drugs are often more life-threatening than the diabetic condition itself.

Consequently, there is a need in the art for a method of lowering blood sugar levels without requiring the injection of human insulin.

There is a further need in the art for a method of lowering blood sugar levels without requiring a pancreatic transplant.

There is a further need in the art for a method of lowering blood sugar levels that is effective, yet has little or no side effects.

There is a further need in the art for a method of lowering blood sugar levels that is inexpensive to administer.

There is a further need in the art for a method of lowering blood sugar levels that provides a consistent and safe leveling of blood glucose levels.

However, in view of the prior art in at the time the present invention was made, it was not obvious to those of ordinary skill in the pertinent art how the identified needs could be fulfilled.

SUMMARY OF THE INVENTION

The scientific name for the sea grape is *coccoloba uvifera*. Its botanical classification is within the polygonaceae family. *Coccoloba uvifera* is found in southern Florida and many warm areas of tropical America and the West Indies. In size it varies from a low shrub along coastal areas to a spreading tree up to 35 feet high. Its leaves are large and leathery growing to 10–20 centimeters wide.

The chemical composition of the *coccoloba uvifera* leaves is broken down as follows:

| Chemical | Concentration | Known Applications |
| --- | --- | --- |
| Alpha-Amyrin | 20,300 ppm | Antitumor; Cytotoxic. |
| Chrysophanol | 25,000 ppm | Antiseptic; Beactericide; Candidicde; Cathartic; Hemostat; Pigment JBH; Purgative; Termitifuge. |
| Emodin | 37,500 ppm | Antiaggregant; Antifeedant; Antiinflammatory; Antispasmodic; Antitumor (Breast); Antiulcer; Cathartic; Cytotoxic; Gonadotropic; Immunosuppressive; Purgative; Styptic; Vasorelaxant; Viricide. |
| Physcion | 23,500 ppm | Antiseptic; Cathartic; Purgative. |
| Rhein | 21,500 ppm | Anticarcinomic; Antiseptic; Antitumor; Bactericide; Candidicide; Cathartic; Cytotoxic; Fungicide; Proteinase-Inhibitor; Purgative; Viricide. |
| Royleanone | 25,350 ppm | |
| Beta-Sitosterol | 17,750 ppm | Androgenic; Anorexic; Antiadenomic; Antiandrogenic; Antiestrogenic; Antifeedant; Antifertility; Antigonadotrophic; Antihyperlipoproteinameic; Antiinflammatory; Antileukemic; Antimutagenic; Antiphidic; Antiprogestational; Antiprostatadenomic; Antiprostatitic; Antitumor; Artemicide; Bactericide; Cancer-Prevantive; Candidicide; Estrogenic; Gonadotrophic; Hepatopprotective; Hypocholesterolemic; Hypoglycemic; Hypolipidemic; Spermicide; Ubiguict; Viricide. |

Use of *Coccoloba uvifera* for the treatment of diabetes was heretofore unknown. However, case studies indicate an effective treatment of the diabetic condition by the daily ingestion of a tea brewed from *Coccoloba uvifera* leaves. Normal serum glucose levels range from 110–130 mg per liter.

Patient A monitored his blood sugar level twice a day, in the morning and the afternoon. Patient A was administered 20 ml of Glucophase and 10 ml of Glucatrol every morning. In the evening, Patent A was administered 10 ml of Glucatrol. Before treatment with a solution brewed from *Coccoloba uvifera* leaves, Patient A's blood sugar levels were as follows:

TABLE 1

(Patient A before treatment)

| Day | 1 | 2 | 3 | 4 | 5 | 6 | 7 | 8 | 9 | 10 | 11 | 12 | 13 | 14 |
| --- | --- | --- | --- | --- | --- | --- | --- | --- | --- | --- | --- | --- | --- | --- |
| AM | 122 | 189 | 168 | 231 | 214 | 194 | 182 | 165 | 189 | 271 | 191 | 169 | 211 | 166 |
| PM | 126 | 194 | 171 | 216 | 187 | 176 | 192 | 167 | 166 | 189 | 184 | 171 | 174 | 167 |

Patient A averaged blood sugar levels of 190.14 in the morning and 177.14 in the evening. Patient A was then administered at least four glasses of a solution brewed from *Coccoloba uvifera* leaves totaling approximately one liter per day with the following results:

TABLE 2

(Patient A after treatment)

| Day | 15 | 16 | 17 | 18 | 19 | 20 | 21 | 22 | 23 | 24 | 25 | 26 | 27 | 28 |
| --- | --- | --- | --- | --- | --- | --- | --- | --- | --- | --- | --- | --- | --- | --- |
| AM | 153 | 180 | 151 | 124 | 262 | 189 | 176 | 125 | 142 | 129 | 158 | 158 | 122 | 141 |
| PM | 140 | 153 | 112 | 155 | 143 | 142 | 125 | 141 | 139 | 131 | 141 | 130 | 130 | 129 |

After just two weeks of treatment, morning blood sugar levels dropped from an average of 190.14 to 157.86. Evening blood sugar levels dropped from an average of 177.14 to 136.50. Patient A noted having no ill effects whatsoever from the addition of the solution brewed from *Coccoloba uvifera* leaves to his treatment plan.

Patient B had been diabetic for 20 years and on and off insulin dependent for the last 17 years. She had been treating her diabetes with Diabeta, usually 3–4 times per day. Unlike Patient A, Patient B only monitored her blood sugar level once per day. Before treatment with a solution brewed from *Coccoloba uvifera* leaves, Patient B's blood sugar levels were as follows:

TABLE 3

(Patient B before treatment)

| Day | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| BS | 164 | 122 | 138 | 80 | 134 | 128 | 95 | 101 | 148 | 174 | 156 | 131 | 162 | 140 |
| Units Insulin AM | 20 | 0 | 0 | 0 | 20 | 0 | 0 | 0 | 20 | 20 | 20 | 20 | 20 | 20 |
| Units Insulin PM | 10 | 0 | 0 | 0 | 10 | 0 | 0 | 0 | 10 | 10 | 10 | 10 | 10 | 10 |
| Diabeta | 2 | 3 | 2 | 0 | 3 | 3 | 2 | 0 | 0 | 0 | 0 | 0 | 0 | 0 |

Patient B averaged blood sugar levels of 133.79 with regular dosages of medication or human insulin injections. Patient B was then administered two (2) to three (3), 240 ml glasses of a solution brewed from *Coccoloba uvifera* leaves per day with the following results:

TABLE 4

(Patient B after treatment)

| Day | 15 | 16 | 17 | 18 | 19 | 20 | 21 | 22 | 23 | 24 | 25 | 26 | 27 | 28 |
|---|---|---|---|---|---|---|---|---|---|---|---|---|---|---|
| BS | 132 | 128 | 90 | 94 | 102 | 92 | 90 | 104 | 98 | 96 | 89 | 94 | 90 | 99 |
| Units Insulin AM | 20 | 0 | 0 | 0 | 0 | 0 | 0 | 0 | 0 | 0 | 0 | 0 | 0 | 0 |
| Units Insulin PM | 10 | 0 | 0 | 0 | 0 | 0 | 0 | 0 | 0 | 0 | 0 | 0 | 0 | 0 |
| Diabeta | 0 | 0 | 0 | 0 | 0 | 0 | 0 | 0 | 0 | 0 | 0 | 0 | 0 | 0 |

After just two weeks of treatment, blood sugar levels dropped from an average of 133.79 to 99.71. Human insulin injections and other medications were no longer required after the first day of treatment with the solution brewed from *Coccoloba uvifera* leaves. Patient B reported feeling better after taking the solution and had enhanced energy levels. The apparent effect on serum glucose levels of the solution brewed from *Coccoloba uvifera* leaves is regulatory and not simply a linear reduction. Long term use by patients in high quantities of over 1.2 liters per day have produced no observable side effects or excess lowering of serum glucose levels.

However, it should be noted that close monitoring is essential when a patient utilizes medications concurrently. The rapid reduction in serum glucose levels by the solution brewed from *Coccoloba uvifera* leaves is often unexpected by medication-dependent patients. Accordingly, those patients must be careful not to excessively lower serum glucose levels by medication when the solution brewed from *Coccoloba uvifera* leaves has already lowered serum glucose levels independently. If serum glucose levels are not carefully monitored and the patient continues to take traditional medications, there is a risk that the patient could dangerously lower his or her serum glucose level (i.e., hyperinsulinism). When hyperinsulinism occurs, glucose is sharply depleted in the process of conversion to glycogen in the liver and muscles and to fat in the adipose tissues.

The present invention solves significant problems in the art by providing a method of treating diabetes in a patient comprising the steps of administering a first quantity of an ingestible medium of *coccoloba uvifera* leaf extract to the patient, monitoring the patient's change in serum glucose level, and modifying, if needed, the first quantity of the ingestible medium of *coccoloba uvifera* leaf extract wherein the patient's serum glucose level is reduced to normal levels. Normal levels are generally considered to be about 110 to 130 mg serum glucose per liter. Accordingly, monitoring and adjustment in the dosages of the ingestible medium of *coccoloba uvifera* leaf extract are increased until the patient's serum glucose level is reduced to 130 mg per liter or less. The patient's serum glucose level may be monitored daily or twice daily depending on the severity of the patient's condition.

While the ingestible medium of *coccoloba uvifera* leaf may be ingested daily, dosages may be staggered to several times a week provided the patient's condition is properly monitored.

In a preferred embodiment, the ingestible medium of *coccoloba uvifera* leaf extract is an aqueous solution created by steps comprising harvesting a quantity of *coccoloba uvifera* leaves, immersing the quantity of *coccoloba uvifera* leaves in a quantity of water, and heating the quantity of water to its boiling point for about 4 hours. The time spent "brewing" the leaf may be just enough to dissolve compounds from the leaf, or may be extended longer as desired. The active compounds within the *coccoloba uvifera* leaves are both resistant to extended high temperatures as well as low pH conditions as found in the human stomach. A particular benefit of the active compounds within the *coccoloba uvifera* leaves is that they can be ingested orally. Insulin, on the other hand, cannot withstand the low pH conditions within the stomach and therefore must be injected with some inherent discomfort to the patient.

The quantity of *coccoloba uvifera* leaves immersed into the quantity of water is recommended to be in a ratio of at least one green leaf to every 3.8 liters of water. In a preferred embodiment, the quantity of *coccoloba uvifera* leaves immersed into the quantity of water is in a ratio of about 4 green leaves to every 3.8 liters of water.

An alternative method of creating the ingestible medium of *coccoloba uvifera* leaf extract comprises the steps of harvesting a quantity of *coccoloba uvifera* leaves and dehydrating the pulp into a tea. In a preferred embodiment, about 15 ml of the tea is dissolved into about 3.8 liters of water before being ingested by the patient.

It should be noted that while the aqueous solution is the preferred method of providing the ingestible medium of *coccoloba uvifera* leaf extract, other forms of oral ingestion may include tablets, capsules, time-released capsules, powders, seasonings, and the like. In addition, other methods of delivery may include transdermal patches, inhalation, intravenous injection, intramuscular injection, and subcutaneous injection. Alternative methods of delivery such as those described above may be necessary in the event that the patient is not capable of taking the *coccoloba uvifera* leaf extract orally, such as in the case of a diabetic coma.

Accordingly, it is an object of the present invention to provide a method of lowering serum glucose levels without requiring the injection of human insulin.

It is another object of the present invention to provide a method of lowering serum glucose levels without requiring a pancreatic transplant.

It is another object of the present invention to provide a method of lowering serum glucose levels that is effective, yet has little or no side effects.

It is another object of the present invention to provide a method of lowering serum glucose levels that is inexpensive to administer.

It is another object of the present invention to provide a method of lowering serum glucose levels that provides a consistent and safe leveling of blood glucose levels.

An advantage of the invention is that the *coccoloba uvifera* leaf extract can withstand the digestive processes of the stomach or intestines and therefore can be given orally.

Another advantage of the invention is the lack of toxic side effects even from high dosages.

Another advantage of the invention is that it is relatively simple to process and administer to a patient.

Another advantage of the invention is that it is inexpensive in comparison to many other drugs used to control serum glucose levels.

Another advantage of the invention is its ability to effectively reduce serum glucose levels without the risk of hyperinsulinism.

These and other important objects, advantages, and features of the invention will become clear as this description proceeds.

The invention accordingly comprises the features of construction, combination of elements, and arrangement of parts that will be exemplified in the above description and the scope of the invention will be indicated in the claims.

It will be seen that the objects set forth above, and those made apparent from the foregoing description, are efficiently attained and since certain changes may be made in the above construction without departing from the scope of the invention, it is intended that all matters contained in the foregoing description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating diabetes in a patient comprising:
   a) preparing a medium of *Coccoloba uvifera* by the steps comprising:
      i) harvesting a quantity of *Coccoloba uvifera* leaves;
      ii) immersing the quantity of *Coccoloba uvifera* leaves in a quantity of water; and
      iii) heating the quantity of water to its boiling point for about 4 hours; and
   b) administering a first quantity of the medium resulting from step (iii) to the patient, and
   c) monitoring the patient's change in serum glucose level, and
   d) modifying, if needed, the first quantity of the medium such that a dosage effective to reduce the patient's serum glucose level is administered thereafter.

2. A method according to claim 1, wherein dosages of said medium of *Coccoloba uvifera* leaf extract are increased until said patient's serum glucose level is reduced to 130 mg per liter or less.

3. A method according to claim 1, wherein said medium of *Coccoloba uvifera* leaf extract is injected intravenously.

4. A method according to claim 1, wherein said medium of *Coccoloba uvifera* leaf extract is injected intramuscularly.

5. A method according to claim 1, wherein said medium of *Coccoloba uvifera* leaf extract is injected subcutaneously.

6. A method according to claim 1, wherein said medium of *Coccoloba uvifera* leaf extract is administered transdermally.

7. A method according to claim 1, wherein said medium of *Coccoloba uvifera* leaf extract is inhaled.

8. A method of treating diabetes in a patient comprising:
   a) preparing an ingestible medium of *Coccoloba uvifera* by the steps comprising:
      i) harvesting a quantity of *Coccoloba uvifera* leaves;
      ii) immersing the quantity of *Coccoloba uvifera* leaves in a quantity of water; and
      iii) heating the quantity of water to its boiling point for about 4 hours; and
   b) administering a first quantity of the medium resulting from step (iii) to the patient, and
   c) monitoring the patient's change in serum glucose level, and
   d) modifying, if needed, the first quantity of the medium such that a dosage effective to reduce the patient's serum glucose level is administered thereafter.

9. A method according to claim 8, wherein dosages of said ingestible medium of *Coccoloba uvifera* leaf extract are increased until said patient's serum glucose level is reduced to 130 mg per liter or less.

10. A method according to claim 8, wherein said patient's serum glucose level is monitored daily.

11. A method according to claim 8, wherein said patient's serum glucose level is monitored twice daily.

12. A method according to claim 8, wherein said ingestible medium of *Coccoloba uvifera* leaf extract is ingested at least three times per week.

13. A method according to claim 8, wherein said ingestible medium of *Coccoloba uvifera* leaf extract is ingested daily.

14. A method according to claim 8, wherein, between steps (i) and (ii), the preparation of the ingestible medium further comprises the steps of dehydrating said quantity of *Coccoloba uvifera* leaves after harvesting and grinding said dehydrated quantity of *Coccoloba uvifera* leaves.

15. A method according to claim 8, wherein said quantity of *Coccoloba uvifera* leaves is immersed into said quantity of water in a ratio of at least one green leaf to every 3.8 liters of water.

16. A method according to claim 8, wherein said quantity of *Coccoloba uvifera* leaves is immersed into said quantity of water in a ratio of about 4 green leaves to every 3.8 liters of water.

17. A method of treating diabetes in a patient comprising:
   a) preparing a solid form ingestible medium of *Coccoloba uvifera* by the steps comprising:
      i) harvesting a quantity of *Coccoloba uvifera* leaves and preparing a pulp therefrom; and
      ii) dehydrating the pulp into a tea; and
   b) administering a first quantity of the medium resulting from step (ii) to the patient, and
   c) monitoring the patient's change in serum glucose level, and
   d) modifying, if needed, the first quantity of the medium such that a dosage effective to reduce the patient's serum glucose level is administered thereafter.

18. A method according to claim 17, wherein about 15 ml of said tea is dissolved into about 3.8 liters of water before being ingested by said patient.

19. A method according to claim 8, wherein said ingestible medium of *Coccoloba uvifera* leaf extract is provided in tablet form.

20. A method according to claim 8, wherein said ingestible medium of *Coccoloba uvifera* leaf extract is provided in a time-release capsule.

* * * * *